(12) United States Patent
Le Coent et al.

(10) Patent No.: US 6,204,226 B1
(45) Date of Patent: Mar. 20, 2001

(54) MIXTURE OF ALKYL-PHENYL-SULFONATES OF ALKALINE EARTH METALS, ITS APPLICATION AS AN ADDITIVE FOR LUBRICATING OIL, AND METHODS OF PREPARATION

(75) Inventors: Jean-Louis Le Coent; Olivier Pascal Marie Clement, both of Le Havre; Amedee Guellec, Saint Sauveur d'Emalleville, all of (FR); William Frank King, Novato, CA (US); Richard J. Nelson, Pinole, CA (US); Steven G. Lockett, San Rafael, CA (US)

(73) Assignees: Chevron Oronite S.A. (FR); Chevron Oronite Co. LLC, San Francisco, CA (US)

( * ) Notice: Subject to any disclaimer, the term of this patent is extended or adjusted under 35 U.S.C. 154(b) by 0 days.

(21) Appl. No.: 09/324,681

(22) Filed: Jun. 3, 1999

(51) Int. Cl.$^7$ ..................... C10M 135/10; C10M 159/24
(52) U.S. Cl. ............................................. 508/390; 508/391
(58) Field of Search ...................................... 508/390, 391

(56) References Cited

U.S. PATENT DOCUMENTS

| | | | |
|---|---|---|---|
| 4,259,193 | * | 3/1981 | Tirtiaux et al. ........................ 508/390 |
| 5,089,155 | * | 2/1992 | Marsh et al. .......................... 508/391 |
| 5,112,506 | * | 5/1992 | Marsh et al. .......................... 508/391 |
| 5,137,648 | * | 8/1992 | Marsh et al. .......................... 508/391 |
| 5,792,732 | * | 8/1998 | Jao et al. .............................. 508/391 |

FOREIGN PATENT DOCUMENTS 2 564 830    11/1985    (FR) ............................ C07C/143/24

* cited by examiner

*Primary Examiner*—Jacqueline V. Howard
(74) *Attorney, Agent, or Firm*—Walter L. Stumpf

(57) ABSTRACT

Mixture of alkyl phenyl sulfonates of alkaline earth metals having: (a) from 20% to 70% by weight of a linear mono alkyl phenyl sulfonate in which the linear mono alkyl substituent contains from 14 to 40 carbon atoms, preferably from 20 to 24 carbon atoms, and the mole % of the phenyl sulfonate radical fixed on position 1 or 2 of the linear alkyl chain is between 10% and 25%, preferably between 13% and 20%, and (b) from 30% to 80% by weight of a branched mono alkyl phenyl sulfonate in which the branched mono alkyl substituent contains from 14 to 18 carbon atoms.

15 Claims, No Drawings

MIXTURE OF ALKYL-PHENYL-SULFONATES OF ALKALINE EARTH METALS, ITS APPLICATION AS AN ADDITIVE FOR LUBRICATING OIL, AND METHODS OF PREPARATION

The present invention relates to a mixture of alkyl phenyl sulfonates of alkaline earth metals, its application as detergent/dispersant additives for lubricating oils, and methods for preparing said mixture.

BACKGROUND OF THE INVENTION

In prior art, methods are known for preparing weakly or strongly superalkalinized sulfonates from sulfonic acids obtained by the sulfonation of different alkyl aryl hydrocarbons and from an excess of alkaline earth base.

The alkyl aryl hydrocarbons subjected to the sulfonation reaction are obtained by alkylation via the Friedel and Craft reaction of different aryl hydrocarbons, particularly aromatic, with two different types of olefin:

Branched olefins obtained by the oligo-polymerization of propylene to $C_{15}$ to $C_{42}$ hydrocarbons, particularly the propylene tetrapolymer dimerized to a $C_{24}$ olefin, and Linear olefins obtained by the oligo-polymerization of ethylene to $C_{14}$ to $C_{40}$ hydrocarbons.

It is easy to obtain a good dispersion in the medium of the alkaline earth base not fixed in the form of salt if the sulfonic acid is derived from a hydrocarbon obtained by alkylation of an aryl hydrocarbon with a branched olefin. It is difficult if the alkylation is effected with a linear olefin. It is particularly difficult for the alkylation of an aryl hydrocarbon where a high percentage of the alkylaryl hydrocarbon has the aryl substituent on positions 1 and 2 of the linear alkyl chain, due to the formation of a skin in the open air.

This poor dispersion is especially pronounced if the medium also contains a high proportion of sulfonate, that is if it corresponds to a low Base Number (between 3 and 60), hence to a low content of free lime and the absence of carbon dioxide and carbonate.

In fact, during the alkylation reaction with benzene or another aromatic or aryl hydrocarbon, 25 mole % of the alkylaryl hydrocarbon has the aryl substituent on positions 1 and 2 of the linear alkyl chain.

When prepared by the method described, for example in French Patent No. 2,564,830, this high proportion of alkyl aryl hydrocarbon having an aryl radical on position 1 or 2 of the linear alkyl chain results in a sulfonate that exhibits hygroscopic properties such that a superficial 'skin' is formed. This 'skin' makes this product unacceptable as an additive for lubricating oil.

Furthermore, the formation of this superficial skin is generally accompanied by a very low filtration rate, a high viscosity, a low incorporation of calcium, a deterioration of anti-rust performance, and an undesirable turbid appearance, or even sedimentation, when the sulfonate thus prepared is added at the rate of 10% by weight to a standard lubricating oil and stored for examination.

The Applicant has carried out chromatographic analyses to identify each of the different isomers differing by the position of the aryl radical on the carbon atom of the linear alkyl chain, and examined their respective influence on the properties of the corresponding alkyl aryl sulfonates of alkaline earth metals obtained from these different isomers.

The Applicant has thus discovered that he could overcome the aforementioned drawbacks, inasmuch as the mole % of the aryl hydrocarbon, other than benzene, having the aryl substituent on positions 1 or 2 of the linear alkyl chain was between 0 and 13%, and preferably between 5 and 11%, and more particularly between 7 and 10%.

This discovery was the subject of a French Patent Application filed Mar. 8, 1995 under No. 95 02,709 by the Applicant.

Yet the Applicant had not succeeded in obtaining satisfactory results when the aryl hydrocarbon was benzene, because, heretofore, he had never been able to prevent the formation of the skin with the use of this aromatic hydrocarbon, even if the hydrocarbon was alkylated with a very long chain linear mono olefin so that the mole % of the aryl hydrocarbon having the aryl substituent on positions 1 or 2 of the linear alkyl chain was between 0 and 13%, and preferably between 5 and 11%, and more particularly between 7 and 10%.

As a result of more intensive studies, the Applicant had discovered that the aforementioned drawbacks could be overcome by using a mixture of alkyl aryl sulfonates of superalkalinized alkaline earth metals comprising:

(a) from 50% to 85% of a linear mono-alkyl phenyl sulfonate in which the linear alkyl chain contains between 14 and 40 carbon atoms, and between 0 and 13 mole % of the phenyl sulfonate radical of the alkaline earth metal is fixed on position 1 or 2 of the linear alkyl chain, and (b) from 15% to 50% of a heavy alkyl aryl sulfonate selected from:
  (i) dialkyl aryl sulfonates wherein both alkyl substituents are linear alkyl chains, of which the sum of the carbon atoms is from 16 to 40, or
  (ii) mono or polyalkyl aryl sulfonates wherein the alkyl substituent or substituents are branched chains, wherein the sum of the carbon atoms is from 15 to 48 carbon atoms.

This mixture of alkyl aryl sulfonates has a maximum of 10 mole % of the phenyl sulfonate radical of the alkaline earth metal fixed on position 1 or 2 of the linear alkyl chain. This mixture has no skin formation after three days of storage in an open jar at room temperature. It has good calcium incorporation, a low viscosity, good solubility, and good performances. This discovery was the subject of a French Patent Application filed Sep. 5, 1996 under No. 96 10,833 by the Applicant.

According to that process, the linear mono-alkyl phenyl sulfonates should have no more than 13% attachment in position 1 or 2. Such low levels of attachment in the 1 or 2 position is possible using a staged HF catalyst alkylation reaction (two reactors in serial; low molar excess of benzene in the first reactor, large molar excess in the second), but it is not possible if only one reactor is available.

SUMMARY OF THE INVENTION

The present invention provides a mixture of alkyl phenyl sulfonates of alkaline earth metals having low color and no skin formation even after three days of storage in an open jar at room temperature.

That mixture is characterized in that it comprises from 20% to 70% by weight of a linear mono alkyl phenyl sulfonate and from 30% to 80% by weight of a branched mono alkyl phenyl sulfonate. This mixture is useful as a detergent/dispersant additive for lubricating oils. Preferably, the Base Number of this mixture is between 3 and 60, and more preferably it is between 10 and 40.

The linear mono alkyl substituent of the linear mono alkyl phenyl sulfonate contains from 14 to 40 carbon atoms, preferably from 20 to 24 carbon atoms. The mole % of the phenyl sulfonate radical fixed on position 1 or 2 of the linear alkyl chain is between 10% and 25%, preferably between 13% and 20%.

The branched mono alkyl substituent of the branched mono alkyl phenyl sulfonate contains from 14 to 18 carbon atoms. The resulting molecular weight of the starting alkylate is low, 300 or less. Preferably, the branched mono alkyl phenyl sulfonate is derived from a polymer of propylene.

One method for preparing this mixture of alkyl aryl sulfonates of alkaline earth metal is by the mixing of the corresponding linear mono alkyl phenyl and branched mono alkyl phenyl, the sulfonation of the mixture of mono alkyl phenyls, and the reaction of the resulting sulfonic acids with an excess of alkaline earth base.

Another method for preparing this mixture of alkyl aryl sulfonates of alkaline earth metal is by the separate preparation of each of the alkyl aryl sulfonic acids, their mixing, and their reaction with an excess of base.

A third method for preparing this mixture of alkyl aryl sulfonates of alkaline earth metal is by the separate preparation of each of the alkyl aryl sulfonates entering into the composition of the mixtures and their mixing in the requisite proportions.

DETAILED DESCRIPTION OF THE INVENTION

In its broadest aspect, the present invention involves a mixture of alkyl phenyl sulfonates of alkaline earth metals, its application as detergent/dispersant additives for lubricating oils, and methods for preparing said mixture.

Prior to discussing the invention in further detail, the following terms will be defined:

DEFINITIONS

As used herein the following terms have the following meanings unless expressly stated to the contrary:

The term "mono alkyl phenyl sulfonate" refers to a phenyl sulfonate having attached thereto one, and only one, alkyl group.

The term "alkaline earth metal" refers to calcium, barium, magnesium, and strontium.

The term "the mole % of the phenyl sulfonate radical fixed on position 1 or 2 of the linear alkyl chain" refers to the mole percentage of all the phenyl sulfonate radicals fixed on the linear alkyl chain that are fixed at the $1^{st}$ and $2^{nd}$ position of the linear alkyl chain.

The term "Base Number" or "BN" refers to the amount of base equivalent to milligrams of KOH in one gram of sample. Thus, higher BN numbers reflect more alkaline products, and therefore a greater alkalinity reserve. The BN of a sample can be determined by ASTM Test No. D2896 or any other equivalent procedure.

Unless otherwise specified, all percentages are in weight percent.

MIXTURE OF ALKYL PHENYL SULFONATES

The mixture of alkyl phenyl sulfonates of the present invention is characterized in that it comprises from 20% to 70% by weight of a linear mono alkyl phenyl sulfonate and from 30% to 80% by weight of a branched mono alkyl phenyl sulfonate. This mixture is useful as a detergent/dispersant additive for lubricating oils. Preferably, the Base Number of this mixture is between 3 and 60, and more preferably it is between 10 and 40.

Linear Mono Alkyl Phenyl Sulfonates

The linear mono alkyl substituent of the linear mono alkyl phenyl sulfonate contains from 14 to 40 carbon atoms, preferably from 20 to 24 carbon atoms. The mole % of the phenyl sulfonate radical fixed on position 1 or 2 of the linear alkyl chain is between 10% and 25%, preferably between 13% and 20%. French Patent No. 2.564.830 to the company Orogil, the former name of the Assignee, and whose corresponding application was published in 1985, and which corresponds to U.S. Pat. No. 4,764,295 describes alkylaryl sulfonates of alkaline earth metals resulting from alkylation by a linear olefin.

Branched Mono Alkyl Phenyl Sulfonate

The branched mono alkyl substituent of the branched mono alkyl phenyl sulfonate contains from 14 to 18 carbon atoms. The resulting molecular weight of the starting alkylate is low, 300 or less. Preferably, the branched mono alkyl phenyl sulfonate is derived from a polymer of propylene.

Mixture of Alkyl-Aryl-Sulfonates

In one embodiment, this mixture of alkyl phenyl sulfonates of alkaline earth metal is prepared by the mixing of the corresponding linear mono alkyl phenyl and branched mono alkyl phenyl, the sulfonation of the mixture of mono alkyl phenyls, and the reaction of the resulting sulfonic acids with an excess of alkaline earth base.

In another embodiment, this mixture of alkyl aryl sulfonates of alkaline earth metal is prepared by the separate preparation of each of the alkyl aryl sulfonic acids, their mixing, and their reaction with an excess of base.

In a third embodiment, this mixture of alkyl aryl sulfonates of alkaline earth metal is prepared by the separate preparation of each of the alkyl aryl sulfonates entering into the composition of the mixtures and their mixing in the requisite proportions.

OTHER ADDITIVE COMPONENTS

The following additive components are examples of components that can be favorably employed in combination with the mixture of alkyl aryl sulfonates of alkaline earth metals in the compositions of the present invention:

(1) Ashless dispersants: alkenyl succinimides, alkenyl succinimides modified with other organic compounds, and alkenyl succinimides modified with boric acid, alkenyl succinic ester.

(2) Oxidation inhibitors:
1) Phenol type phenolic) oxidation inhibitors: 4,4'-methylenebis (2,6-di-tert-butylphenol),4,4'-bis(2,6-di-tert-butylphenol),
4,4'-bis(2-methyl-6-tert-butylphenol),2,2'-(methylenebis(4-methyl-6-tert-butyl-phenol),
4,4'-butylidenebis(3-methyl-6-tert-butylphenol),
4,4'-isopropylidenebis(2,6-di-tert-butylphenol),
2,2'-methylenebis(4-methyl-6-nonylphenol),
2,2'-isobutylidene-bis(4,6-dimethylphenol),
2,2'-methylenebis(4-methyl-6-cyclohexylphenol),
2,6-di-tert-butyl4-methylphenol, 2,6-di-tert-butyl4-ethylphenol,
2,4-dimethyl-6-tert-butyl-phenol,
2,6-di-tert-α-dimethylamino-p-cresol, 2,6-di-tert-4 (N.N' dimethylaminomethylphenol),4,4'-thiobis(2-methyl-6-tert-butylphenol), 2,2'-thiobis(4-methyl-6-tert-butylphenol),
bis(3-methyl-4-hydroxy-5-tert-butylbenzyl)-sulfide, and bis (3,5-di-tert-butyl4-hydroxybenzyl).
2) Diphenylamine type oxidation inhibitor: alkylated diphenylamine, phenyl-α-naphthylamine, and alkylated α-naphthylamine.

3) Other types: metal dithiocarbamate (e.g., zinc dithiocarbamate), and methylenebis(dibutyldithiocarbamate).

(3) Rust inhibitors (Anti-rust agents):
1) Nonionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.
2) Other compounds: stearic acid and other fatty acids, dicarboxilic acids, metal soaps, fatty acid amine salts, metal salts of heavy sulfonic acid, partial carboxylic acid ester of polyhydric alcohol, and phosphoric ester.

(4) Demulsifiers: addition product of alkylphenol and ethyleneoxide, poloxyethylene alkyl ether, and polyoxyethylene sorbitane ester.

(5) Extreme pressure agents (EP agents): zinc dialkyldithiophosphate (Zn-DTP, primary alkyl type & secondary alkyl type), sulfurized oils, diphenyl sulfide, methyl trichlorostearate, chlorinated naphthalene, benzyl iodide, fluoroalkylpolysiloxane, and lead naphthenate.

(6) Friction modifiers: fatty alcohol, fatty acid, amine, borated ester, and other esters (7) Multifunctional additives: sulfurized oxymolybdenum dithiocarbamate, sulfurized oxymolybdenum organo phosphoro dithioate, oxymolybdenum monoglyceride, oxymolybdenum diethylate amide, amine-molybdenum complex compound, and sulfur-containing molybdenym complex compound (8) Viscosity Index improvers: polymethacrylate type polymers, ethylene-propylene copolymers, styrene-isoprene copolymers, hydrated styrene-isoprene copolymers, polyisobutylene, and dispersant type viscosity index improvers.

(9) Pour point depressants: polymethyl methacrylate.

(10) Foam Inhibitors: alkyl methacrylate polymers and dimethyl silicone polymers.

OIL OF LUBRICATING VISCOSITY

The oil of lubricating viscosity used in such compositions may be mineral oil or synthetic oils of viscosity suitable for use in the crankcase of an internal combustion engine, such as gasoline engines and diesel engines, including passenger car, heavy duty on-road and off-road, railroad, natural gas and marine, such as trunk piston and slow speed crosshead. Crankcase lubricating oils ordinarily have a viscosity of about 1300 cSt 0° F. to 24 cSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity, such as didodecyl benzene, can be used. Useful synthetic esters include the esters of both monocarboxylic acids and polycarboxylic acids, as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acids and mono and dihydroxy alkanols can also be used. Blends of mineral oils with synthetic oils are also useful. For example, blends of 10% to 25% hydrogenated 1-trimer with 75% to 90% 150 SUS (100° F.) mineral oil gives an excellent lubricating oil base.

LUBRICATING OIL COMPOSITIONS

The additives produced by the process of this invention are useful for imparting detergency and dispersancy properties to the lubricating oil. When employed in this manner, the amount of the mixture of alkyl phenyl sulfonates of alkaline earth metals ranges from about 0.5% to 40% of the total lubricant composition, although preferably from about 1% to 25% of the total lubricant composition. Such lubricating oil compositions are useful in the crankcase of an internal combustion engine, such as gasoline engines and diesel engines, including passenger car, heavy duty on-road and off-road, railroad, natural gas and marine, such as trunk piston and slow speed crosshead. They are also useful in hydraulic applications.

The lubricating oil composition can be used in a method of decreasing black sludge deposits, a method of decreasing piston deposits, or both.

Such lubricating oil compositions employ a finished lubricating oil, which may be single or multigrade. Multigrade lubricating oils are prepared by adding viscosity index (VI) improvers. Typical VI improvers are polyalkyl methacrylates, ethylene-propylene copolymers, styrene-diene copolymers, and the like. So-called dispersant VI improvers, which exhibit dispersant properties as well as VI modifying properties, can also be used in such formulations.

In one embodiment, a lubricating oil composition would contain (a) a major amount of an oil of lubricating viscosity;

(b) from 0.5% to 40% of the mixture of mono alkyl phenyl sulfonates of alkaline earth metals of the present invention;

(c) from 0% to 20% of at least one ashless dispersant;

(d) from 0% to 5% of at least one zinc dithiophosphate;

(e) from 0% to 10% of at least one oxidation inhibitor;

(f) from 0% to 1% of at least one foam inhibitor; and (g) from 0% to 20% of at least one viscosity index improver.

PROCESS FOR PRODUCING A LUBRICATING OIL COMPOSITION

In one embodiment, a lubricating oil composition is produced by blending a mixture of:

(a) a major amount of an oil of lubricating viscosity;

(b) from 0.5% to 40% of the mixture of mono alkyl phenyl sulfonates of alkaline earth metals of the present invention;

(c) from 0% to 20% of at least one ashless dispersant;

(d) from 0% to 5% of at least one zinc dithiophosphate;

(e) from 0% to 10% of at least one oxidation inhibitor;

(f) from 0% to 1% of at least one foam inhibitor; and (g) from 0% to 20% of at least one viscosity index improver.

The lubricating oil composition produced by that method might have a slightly different composition than the initial mixture, because the components may interact. The components can be blended in any order and can be blended as combinations of components.

ADDITIVE CONCENTRATES

Additive concentrates are also included within the scope of this invention. The concentrates of this invention comprise the mixture of alkyl aryl sulfonates of alkaline earth metals of the present, with at least one of the additives disclosed above. Typically, the concentrates contain sufficient organic diluent to make them easy to handle during shipping and storage.

From 10% to 90% of the concentrate is organic diluent. From 0.5% to 90% of concentrate is the mixture of alkyl aryl sulfonates of alkaline earth metals of the present invention. The remainder of the concentrate consists of other additives.

Suitable organic diluents which can be used include for example, solvent refined 100N, i.e., Cit-Con 100N, and hydrotreated 100N, i.e., RLOP 100N, and the like. The organic diluent preferably has a viscosity of from about 1 to about 20 cSt at 100° C.

EXAMPLES OF ADDITIVE PACKAGES

Below are representative examples of additive packages that can be used in a variety of applications. These representative examples employ the novel dispersants of the present invention. The following percentages are based on the amount of active component, with neither process oil nor diluent oil. These examples are provided to illustrate the present invention, but they are not intended to limit it.

Below are representative examples of additive packages that can be used in a variety of applications. These representative examples employ the mixture of alkyl aryl sulfonates of alkaline earth metals of the present invention. The following weight percents are based on the amount of active component, with neither process oil nor diluent oil. These examples are provided to illustrate the present invention, but they are not intended to limit it.

I. MARINE DIESEL ENGINE OILS

| | |
|---|---|
| 1) Mixture of alkyl aryl sulfonates | 65% |
| Primary alkyl Zn-DTP | 5% |
| Oil of lubricating viscosity | 30% |
| 2) Mixture of alkyl aryl sulfonates | 65% |
| Alkenyl succinimide ashless dispersant | 5% |
| Oil of lubricating viscosity | 30% |
| 3) Mixture of alkyl aryl sulfonates | 60% |
| Primary alkyl Zn-DTP | 5% |
| Alkenyl succinimide ashless dispersant | 5% |
| Oil of lubricating viscosity | 30% |
| 4) Mixture of alkyl aryl sulfonates | 65% |
| Phenol type oxidation inhibitor | 10% |
| Oil of lubricating viscosity | 25% |
| 5) Mixture of alkyl aryl sulfonates | 55% |
| Alkylated diphenylamine-type oxidation inhibitor | 15% |
| Oil of lubricating viscosity | 30% |
| 6) Mixture of alkyl aryl sulfonates | 65% |
| Phenol-type oxidation inhibitor | 5% |
| Alkylated diphenylamine-type oxidation inhibitor | 5% |
| Oil of lubricating viscosity | 25% |
| 7) Mixture of alkyl aryl sulfonates | 60% |
| Primary alkyl Zn-DTP | 5% |
| Phenol-type oxidation inhibitor | 5% |
| Oil of lubricating viscosity | 30% |
| 8) Mixture of alkyl aryl sulfonates | 60% |
| Alkenyl succinimide ashless dispersant | 5% |
| Alkylated diphenylamine-type oxidation inhibitor | 10% |
| Oil of lubricating viscosity | 25% |

-continued

| | |
|---|---|
| 9) Mixture of alkyl aryl sulfonates | 55% |
| Other additions | 25% |
| Primary alkyl Zn-DTP | |
| Alkenyl succinic ester ashless dispersant | |
| Phenol-type oxidation inhibitor | |
| Alkylated diphenylamine-type oxidation inhibitor | |
| Oil of lubricating viscosity | 30% |

II. MOTOR CAR ENGINE OILS

| | |
|---|---|
| 1) Mixture of alkyl aryl sulfonates | 25% |
| Alkenyl succinimide ashless dispersant | 35% |
| Primary alky Zn-DTP | 10% |
| Oil of lubricating viscosity | 30% |
| 2) Mixture of alkyl aryl sulfonates | 20% |
| Alkenyl succinimide ashless dispersant | 40% |
| Secondary alkyl Zn-DTP | 5% |
| Dithiocarbamate type oxidation inhibitor | 5% |
| Oil of lubricating viscosity | 30% |
| 3) Mixture of alkyl aryl sulfonates | 20% |
| Alkenyl succinimide ashless dispersant | 35% |
| Secondary alkyl Zn-DTP | 5% |
| Phenol type oxidation inhibitor | 5% |
| Oil of lubricating viscosity | 35% |
| 4) Mixture of alkyl aryl sulfonates | 20% |
| Alkenyl succinimide ashless dispersant | 30% |
| Secondary alkyl Zn-DTP | 5% |
| Dithiocarbamate type anti-wear agent | 5% |
| Oil of lubricating viscosity | 40% |
| 5) Mixture of alkyl aryl sulfonates | 20% |
| Succinimide ashless dispersant | 30% |
| Secondary alkyl Zn-DTP | 5% |
| Molybdenum-containing anti-wear agent | 5% |
| Oil of lubricating viscosity | 40% |
| 6) Mixture of alkyl aryl sulfonates | 20% |
| Alkenyl succinimide ashless dispersant | 30% |
| Other additives | 10% |
| Primary alkyl Zn-DTP | |
| Secondary alkyl Zn-DTP | |
| Alkylated diphenylamine-type oxidation inhibitor | |
| Dithiocarbamate type anti-wear agent | |
| Oil of lubricating viscosity | 40% |
| 7) Mixture of alkyl aryl sulfonates | 60% |
| Other additives | 10% |
| Phenol type oxidation inhibitor | |
| Alkylated diphenylamine-type | |
| Oxidation inhibitor | |
| Dithiocarbamate type anti-wear agent | |
| Demulsifier | |
| Boron-containing friction modifier | |
| Oil of lubricating viscosity | 30% |

III. HYDRAULIC OILS

| | |
|---|---|
| 1) Mixture of alkyl aryl sulfonates | 20% |
| Primary alkyl Zn-DTP | 50% |
| Other additives | 25% |
| Phenol type oxidation inhibitor | |
| Phosphorous-containing extreme pressure agent | |
| Triazol type corrosion inhibitor | |
| Demulsifier | |
| Nonionic anti-rust agent | |
| Oil of lubricating viscosity | 5% |
| 2) Mixture of alkyl aryl sulfonates | 10% |
| Primary alkyl ZN-DTP | 40% |
| Other additives | 47% |
| Phenol type oxidation inhibitor | |
| Sulfur-containing extreme pressure agent | |
| Triazol type corrosion inhibitor | |
| Demulsifier | |
| Nonionic anti-rust agent | |
| Oil of lubricating viscosity | 3% |
| 3) Mixture of alkyl aryl sulfonates | 10% |
| Phosphorous-containing extreme pressure agent | 40% |
| Phenol type oxidation inhibitor | 15% |

-continued

| | |
|---|---|
| Other additives | 25% |
| Diphenylamine type oxidation inhibitor | |
| Sulfur-containing extreme pressure agent | |
| Triazol type corrosion inhibitor | |
| Demulsifier | |
| Nonionic anti-rust agent | |
| Oil of lubricating viscosity | 10% |
| 4) Mixture of alkyl aryl sulfonates | 20% |
| Phosphorous-containing extreme pressure agent | 30% |
| Other additives | 45% |
| Diphenylamine type oxidation inhibitor | |
| Sulfur-containing extreme pressure agent | |
| Triazol type corrosion inhibitor | |
| Demulsifier | |
| Nonionic anti-rust agent | |
| Oil of lubricating viscosity | 5% |
| IV. TRANSMISSION HYDRAULIC FLUIDS | |
| 1) Mixture of alkyl aryl sulfonates | 35% |
| Primary alkyl Zn-DTP | 20% |
| Polyol type friction modifier | 20% |
| Sulfur-containing extreme pressure agent | 5% |
| Oil of lubricating viscosity | 20% |
| 2) Mixture of alkyl aryl sulfonates | 40% |
| Primary alkyl Zn-DTP | 15% |
| Amide type friction modifier | 15% |
| Sulfur-containing extreme pressure agent | 5% |
| Oil of lubricating viscosity | 25% |
| 3) Mixture of alkyl aryl sulfonates | 30% |
| Primary alkyl Zn-DTP | 20% |
| Other additives | 30% |
| Alkenyl succinimide ashless dispersant | |
| Amide type friction modifier | |
| Ester type friction modifier | |
| Phosphorous, Sulfur-containing extreme pressure agent | |
| Oil of lubricating viscosity | 20% |
| 4) Mixture of alkyl aryl sulfonates | 35% |
| Primary alkyl Zn-DTP | 15% |
| Other additives | 25% |
| Polyol type friction modifier | |
| Amide type friction modifier | |
| Phosphorous, Sulfur-containing extreme pressure agent | |
| Oil of lubricating viscosity | 25% |

EXAMPLES

The invention will be further illustrated by following examples, which set forth particularly advantageous method embodiments. While the Examples are provided to illustrate the present invention, they are not intended to limit it.

A) Synthesis of the Alkylate

The alkylate is synthesized in a continuous alkylation pilot plant with hydrofluoric acid (as catalyst). It consists of one reactor of 1.125 litter and a 15 litter settler wherein the organic phase is separated from the phase containing the hydrofluoric acid, all of the equipment being maintained under a pressure of about $3.5 \times 10^5$ Pa.

The organic phase is then withdrawn via a valve and expanded to atmospheric pressure and the benzene is removed by topping, that is heating to 160° C. at atmospheric pressure.

After withdrawal, the mineral phase is neutralized by caustic potash.

The variables of the alkylation reaction are as follows: benzene/olefin mole ratio is between 10 and 2. As the target is to have predominantly a mono-alkylate, there is always a large excess of benzene. The ratio of hydrofluoric acid to the olefin by volume is between 1:1 and 2.5:1.

B) Distillation of the Alkylate

If benzene is alkylated by a $C_{20}$ to $C_{24}$ linear olefin, there is no formation of a light fraction, that is of alkylbenzene, wherein the alkyl radicals is lower than $C_{13}$. Hence it is sufficient to effect a topping of the unreacted benzene to obtain the corresponding alkylate.

In the other case for example if a heavy propylene oligomer (which molecular weight is from 196 to 256) is used a light fraction is produced during the catalytic alkylation reaction, and this fraction must be removed, just like the excess of benzene, on a vacuum distillation column. Light fraction means any alkyl benzene having an alkyl chain lower $C_{13}$. To remove such a light fraction, the final distillation conditions are as follows:

Temperature at top of column: 262° C.

Temperature at bottom of column: 302° C.

Pressure: $187 \times 102$ Pa (187 mbar)

C) Sufonation of the Alkylate

Sulfonation is effected either on the two alkylates separately or either on the mixture of the two alkylates.

The reaction is effected using sulfur trioxide $SO_3$, produced by the passage of a mixture of oxygen and sulfur dioxide $SO_2$ through a catalytic furnace containing vanadium oxide $V_2O_5$.

The gas thus produced is introduced at the top of a sulfonation reactor two meter long and one centimeter diameter in a concurrent alkylate stream. The resulting sulfonic acid is recovered at the bottom of the reactor. The sulfonation conditions are as follows:

$SO_3$/alkylate mole ratio about 1 (from 0.8 to 1.2)

Sulfonation temperature between 50° C. and 60° C.

And with nitrogen as vector gas to dilute the $SO_3$ to 4% by volume

Level of conversion is about 88% and the mineral activity expressed as sulfuric acid is the range 06% –1%. By using a process described in our international patent application PCT/FR 94/01147 filed on Sep. 30, 1994 published on Apr. 3, 1995 under WO 95/09840, the mineral activity is decreased down to 0.30% by a thermal treatment and a dilution by 10% of 100 N.

The analysis given in the table below relative to the embodiments of the present invention correspond to the product obtained after thermal treatment.

D) Synthesis of the Low Overbased Sulfonates

In this step, relative molar proportions of Ca $(OH)_2$ and sulfonic acid obtained in the preceding step are reacted in order to obtain a proportion of 37% of lime non-neutralized by sulfonic acid in the final product. This proportion of 37% of non-neutralized lime makes it possible to obtain a BN 20 in the final sulfonate, according to standard ASTM D 2896.

To achieve this, a quantity of $Ca(OH)_2$ is added which does not correspond to the stoichiometric neutralization of the quantity of sulfonic acid reacted, that is 0.5 mole of $Ca(OH)_2$ per mole of this sulfonic acid, but an excess of $Ca(OH)_2$ is added with respect to this stoichiometric quantity, that is a proportion of 0.73 mole of $Ca(OH)_2$ per mol of sulfonic acid, to obtain a BN of about 20.

The conditions of reaction used are those described in before mentioned French patent application No. 2.564.830 of the company Orogil, the former name of the applicant, and published on Nov. 29, 1985 (in the U.S. Pat. No. 4,764,925—Aug. 16, 1988.).

Tests Used In Examples

Viscosity at 100° C. (cSt):

The viscosity is measured at the temperature of 100° C. after dilution of the product sample to be measured in 100 N oil until a solution is obtained having a total calcium content of 2.35% by weight.

Viscosity is measured following method ASTM D 445.
Compatibility/Solubility:

The method is aimed to evaluate the appearance and of the storage stability of the additive at a concentration of 10% in 600N Neutral diluent oil.

The appearance of the solution is examined after 30 days at ambient temperature.

If appearance of the solution is clear and bright, the result is qualified as good.

If appearance of the solution is cloudy or if there is any deposit by sedimentation, the result is qualified as poor.

Skin Formation:

This test is conducted at room temperature in an open jar of 200 ml where 30 grams of material to be tested is introduced.

If a skin formation appears only at least three days, the material is considered to be "good" not sensitive to water.

If a skin formation appears after 10 hours or one day, the material is considered to be "poor" that means too sensitive to water.

Example 1

In this example, 50% per weight of a linear alkylate obtained by continuous alkylation of benzene by a $C_{20}$ to $C_{24}$ normal alpha olefin (where the charge molar ratio benzene/olefin is 5:1) was mixed with 50% by weight of a branched alkylate obtained by alkylation of benzene by a $C_{15}$–$C_{18}$ heavy propylene oligomer and the removal of benzene and the light aromatic fractions (with alkyl chain lower than $C_{13}$). Sulfonation was effected on the aforementioned mixture of alkylates. The mole % of the phenyl sulfonate radical fixed on position 1 or 2 of the linear alkyl chain was 7.5%.

Example 2

In this example, 65% per weight of a linear alkylate obtained by continuous alkylation of benzene by a $C_{20}$ to $C_{24}$ normal alpha olefin (where the charge molar ratio benzene/olefin is 5:1) was mixed with 35% by weight of a branched alkylate obtained by alkylation of benzene by a $C_{15}$–$C_{18}$ heavy propylene oligomer and the removal of benzene and the light aromatic fractions (with alkyl chain lower than $C_{13}$). Sulfonation was effected on the aforementioned mixture of alkylate. The mole % of the phenyl sulfonate radical fixed on position 1 or 2 of the linear alkyl chain was 9.75%.

Example 3

This example is identical to Example 1 but a higher molar ratio benzene/$C_{20}$–$C_{24}$ normal alpha olefin was used 10:1 instead of 5:1 in the Example 1 and the ratio linear versus branched alkylated was lower 40/60 per weight instead of 50/50. Sulfonation was effected on the aforementioned mixture of alkylates. The mole % of the phenyl sulfonate radical fixed on position 1 or 2 of the linear alkyl chain was 8%.

Example 4

This example is identical to Example 1 but linear alkylate and branched alkylate were sulfonated separately, then the corresponding sulfonic were mixed together and the superalkalinization is effected on the aforementioned mixture of sulfonic acid. The mole % of the phenyl sulfonate radical fixed on position 1 or 2 of the linear alkyl chain was 7.5%.

Example 5

This example is identical to Example 1 but the ratio of linear alkylate and branched alkylate is different: 40 linear/60 branched (per weight) instead of 50/50 per weight in Example 1. The mole % of the phenyl sulfonate radical fixed on position 1 or 2 of the linear alkyl chain was 6%.

Comparative Example A

This example is identical to Example 1 but the ratio of linear alkylate and branched alkylate is different 90 linear/10 branched per weight instead of 50/50 per weight in Example 1. The consequences on the corresponding sulfonates are a smaller incorporation of lime; BN: 15.5 instead of 17.6–19; a higher viscosity and above all, a quicker appearance of skin with gel formation and poor compatibility making it unfit as an additive for lubricant. The mole % of the phenyl sulfonate radical fixed on position 1 or 2 of the linear alkyl chain was 13.5%.

Comparative Example B

A 100% linear alkylate obtained by continuous alkylation of benzene by a $C_2$–$C_{24}$ normal alpha olefin (where the charge molar ratio benzene/olefin is 5:1) is sulfonated and then converted into sulfonates. The mole % of the phenyl sulfonate radical fixed on position 1 or 2 of the linear alkyl chain was 15%.

The consequences on the corresponding sulfonate are a smaller incorporation of lime (BN 14.5 instead of 17.6–19), a higher viscosity, and above all, a quicker appearance of skin with gel formation and poor compatibility, making it unfit as an additive for lubricants.

Comparative Example C

In this example, the sulfonation is effected exclusively on the $C_{15}$ to $C_{18}$ heavy alkylate used in Example 1, in order to determine the influence of the molecular weight. It may be observed that, as in comparative Example 3, the corresponding sulfonate exhibits a superficial skin that makes it difficult for using as an additive for lubricating oil if in the formulation there are no other sulfonates.

The results of those examples is shown in the table below:

| Example | Viscosity at 100° C. | Compatibility/Solubility | Skin Formation |
| --- | --- | --- | --- |
| 1 | 50.6 | Good | 3 days |
| 2 | 36 | Good | 3 days |
| 3 | 45 | Good | 3 days |
| 4 | 48 | Good | 3 days |
| 5 | 36 | Good | 5 days |
| A | 92 | Poor | 1 day |
| B | 100 | Poor | 10 hours |
| C | 97 | Poor | 1 day |

While the present invention has been described with reference to specific embodiments, this application is intended to cover those various changes and substitutions that may be made by those skilled in the art without departing from the spirit and scope of the appended claims.

What is claimed is:

1. Mixture of alkyl phenyl sulfonates of alkaline earth metals characterized in that it comprises
    (a) from 20% to 70% of a linear mono alkyl phenyl sulfonate in which the linear mono alkyl substituent contains from 14 to 40 carbon atoms, and the mole % of the phenyl sulfonate radical fixed on position 1 or 2 of the linear alkyl chain is between 10% and 25, and
    (b) from 30% to 80% of a branched mono alkyl phenyl sulfonate in which the branched mono alkyl substituent contains from 14 to 18 carbon atoms.

2. Mixture according to claim 1, wherein said linear mono alkyl phenyl sulfonate contains from 20 to 24 carbon atoms, and the mole % of the phenyl sulfonate radical fixed on position 1 or 2 of the linear alkyl chain is between 13% and 20%.

3. Mixture as claimed in claim 1 characterized in that the linear mono alkyl phenyl sulfonate defined in (a) of said claim 1 is derived from a $C_{14}$–$C_{40}$ normal alpha olefin.

4. Mixture as claimed in claim 3 characterized in that the linear mono alkyl phenyl sulfonate defined in (a) of said claim 1 is derived from a $C_{20}$–$C_{24}$ normal alpha olefin.

5. Mixture as claimed in claim 1 characterized in that the branched mono alkyl phenyl sulfonate defined in (b) of said claim 1 is derived from a polymer of propylene.

6. Mixture as claimed in claim 1 characterized in that the Base Number of said mixture is between 3 and 60.

7. Mixture as claimed in claim 6 characterized in that the Base Number of said mixture is between 10 and 40.

8. Lubricating oil containing a mixture of alkyl phenyl sulfonates of alkaline earth metal as claimed in claim 1.

9. A lubricating oil formulation comprising:
   (a) a major amount of a base oil of lubricating viscosity;
   (b) from 0.5 to 40% of the mixture of alkyl phenyl sulfonates of alkaline earth metal as claimed in claim 1;
   (c) from 0 to 20% of at least one ashless dispersant;
   (d) from 0 to 5% of at least one zinc dithiophosphate;
   (e) from 0 to 10% of at least one oxidation inhibitor;
   (f) from 0 to 1% of at least one foam inhibitor; and
   (g) from 0 to 20% of at least one viscosity index improver.

10. A concentrate comprising about from 10 weight % to 90 weight % of a compatible organic liquid diluent and about from 0.5 weight % to 90 weight % of the mixture of alkyl phenyl sulfonates of alkaline earth metal as claimed in claim 1.

11. A method of producing a lubricating oil composition comprising blending the following components together:
   (a) a major amount of a base oil of lubricating viscosity;
   (b) from 0.5 to 40% of the mixture of alkyl phenyl sulfonates of alkaline earth metal as claimed in claim 1;
   (c) from 0 to 20% of at least one ashless dispersant;
   (d) from 0 to 5% of at least one zinc dithiophosphate;
   (e) from 0 to 10% of at least one oxidation inhibitor;
   (f) from 0 to 1% of at least one foam inhibitor; and
   (g) from 0 to 20% of at least one viscosity index improver.

12. A lubricating oil composition produced by the method according to claim 11.

13. Method for preparing a mixture of alkyl phenyl sulfonates of alkaline earth metal as claimed in claim 1, characterized by:
   (a) the mixing of the corresponding linear mono alkyl phenyl and branched mono alkyl phenyl,
   (b) the sulfonation of the mixture of mono alkyl phenyls to produce sulfonic acids, and
   (c) the reaction of the resulting sulfonic acids with an excess of alkaline earth base.

14. Method for preparing a mixture of alkyl phenyl sulfonates of alkaline earth metal as claimed in claim 1, characterized by:
   (a) the separate preparation of each of the alkyl phenyl sulfonic acids,
   (b) the mixing of the alkyl phenyl sulfonic acids, and
   (c) the reaction of the resulting sulfonic acids with an excess of alkaline earth base.

15. Method for preparing a mixture of alkyl phenyl sulfonates of alkaline earth metal as claimed in claim 1, characterized by:
   (a) the separate preparation of each of the alkyl phenyl sulfonates entering into the composition of the mixtures, and
   (b) the mixing of the alkyl phenyl sulfonates produced in step (a).

* * * * *